(12) United States Patent
DeLong et al.

(10) Patent No.: US 8,575,374 B1
(45) Date of Patent: Nov. 5, 2013

(54) IONIC LIQUIDS PROCESSING OF BIOMASS TO REDUCING SUGARS AND OTHER DEHYDRATION PRODUCTS

(76) Inventors: Hugh C. DeLong, Waldorf, MD (US);
Paul C. Trulove, Annapolis, MD (US);
Robert A. Mantz, Efland, NC (US);
William M. Reichert, Mobile, AL (US);
Jeremy Mandia, Highland, NY (US)

( * ) Notice: Subject to any disclaimer, the term of this patent is extended or adjusted under 35 U.S.C. 154(b) by 199 days.

(21) Appl. No.: 12/908,986

(22) Filed: Oct. 21, 2010

(51) Int. Cl.
*C07D 303/02* (2006.01)
(52) U.S. Cl.
USPC .................................................. 549/548
(58) Field of Classification Search
None
See application file for complete search history.

(56) References Cited

U.S. PATENT DOCUMENTS 8,030,030 B2 * 10/2011 Varanasi et al. ............... 435/72

* cited by examiner

*Primary Examiner* — Sun Jae Loewe
(74) *Attorney, Agent, or Firm* — AFMCLO/JAZ; Jeffrey R. Moore

(57) ABSTRACT

The present invention describes the use of an ionic liquid acid catalyst for the hydrolysis of cellulose into reducing sugars and other degradation products. The use of an ionic liquid catalyst for the hydrolysis of cellulose provides a low volatility catalyst and eliminates the hazards associated with the handling of mineral acids. Conditions such as temperature, catalyst modification, and ionic liquid solvent control the production of reducing sugars and other products. The combination of using an ionic liquid as the solvent for cellulose and ionic liquid catalyst provides an unprecedented tunability of the reaction properties giving more control over the conversion process to produce dehydration products with higher yields depending on the desired feedstock.

8 Claims, 5 Drawing Sheets

IONIC LIQUIDS PROCESSING OF BIOMASS TO REDUCING SUGARS AND OTHER DEHYDRATION PRODUCTS

RIGHTS OF THE GOVERNMENT

The invention described herein may be manufactured and used by or for the Government of the United States for all governmental purposes without the payment of any royalty.

BACKGROUND OF THE INVENTION

The invention relates to a process by which biomass (cellulose, hemicelluloses, lignocelluloses, or any combination thereof) can be dissolved and converted into simple reducing sugars (glucose, fructose, glyceraldhyde, lactose, arabinose, and maltose) and other dehydration products using an appropriate ionic liquid solvent and an ionic liquid catalyst.

Cellulose is the most abundant biopolymer in the world and represents a tremendous quantity of stored energy. However, the properties of cellulose (high molecular weight, solid at room temperature, and solubility) greatly limit access to this stored energy. The energy potential of cellulose is essentially locked in the glucose units that make up the biopolymer, and thus the key to using cellulose as a renewable energy source is breaking the β-glycosidic bonds producing reducing sugars which can be used as inexpensive feedstocks in fermentations and hydrogenations leading to non-petroleum based fuels. The obstacle in using cellulose is the low yield of reducing sugars using traditional hydrolysis methods employing either enzymes or mineral acids. The low reactivity of cellulose is due to the hydrogen bonded supramolecular structure of the biopolymer. The structure restricts access to the glycosidic bonds resulting in poor yields. Several methods have been explored to overcome this problem.

The current aqueous based process for conversion of cellulose, purified biomass, to glucose involves a simple hydrolysis carried out in cellulose/water slurry with an enzyme or dilute mineral acid catalyst. These reactions result in the production of glucose in low yields. The reactivity of the cellulose is limited due to its highly crystalline nature. The crystalline regions of cellulose restrict the ability of the catalyst to access the glycosidic bond between the polymer units. The reactivity of the cellulose can be controlled by the ratio of crystalline regions to amorphous regions within the structure of the polymer. A higher crystalline ratio limits the solubility and reactivity of the polymer, since it is the amorphous regions that grant access to the glycosidic bonds. In this way the catalyst slowly degrades the polymer by digesting the amorphous regions first leaving behind an essentially crystalline matrix. One of the major drawbacks to this method is the incomplete digestion of the cellulose resulting in low yields of glucose. Another significant limitation of the use of mineral acids to convert cellulose to glucose is the further degradation of the glucose to products such as hydroxymethylfurfural, levulinic acid and formic acid.

Current methods use a pretreatment of the cellulose before processing to break up some of the crystalline regions increasing the percentage of amorphous regions in the cellulose; this, in turn, speeds up the depolymerization to glucose and improves the overall yield. There are several methods of pretreatment (biological, physical, chemical, and physiochemical) and each has its drawbacks. However these pretreatments are expensive, because they use costly solvents, are energy intensive, or are time consuming. Recently ionic liquid based pretreatment has shown potential as a cost effective alternative to aqueous based pretreatments in both enzymatic hydrolysis as well as acid hydrolysis.

Current use of Ionic Liquids in the Conversion of Cellulose to Reducing Sugars

One of the first applications of ionic liquids in this area was as a pretreatment of cellulose for enzymatic hydrolysis. In the case of A. P. Dadi, S. Varanasi and C. A. Schall, *Biotechnol. Bioeng.*, 2006, 95, 904-910, the pretreatment resulted in amorphous cellulose that exhibited enhanced enzymatic reactivity. Recently ionic liquids have been used as a solvent for cellulose in traditional acid catalyzed hydrolysis. See, e.g., C. Li, Q. Wang and Z. K. Zhao, *Green Chem.*, 2008, 10, 177-182. These studies demonstrated the benefits of using an ionic liquid in the hydrolysis of cellulose. The dissolution of the cellulose allows for increased reaction rates due to the accessibility of the glucosidic bonds in the cellulose. One of the drawbacks to this method is the use of concentrated mineral acid, in one case 98% wt. $H_2SO_4$, which requires care in handling and is volatile. Another report suggested the use of ionic liquids, again as a solvent for cellulose, but with solid acid catalysts for the hydrolysis of cellulose. While the solid catalysts demonstrated the ability to convert cellulose to simple sugars, heterogeneous catalysis can have low yields due to inefficient mixing.

This invention was developed to incorporate the acid site within the ionic liquid structure to provide a homogeneous catalyst. The ionic liquid catalyst structure can be modified to tune the catalytic activity and optimize the product mixture to obtain glucose with very little byproducts produced.

SUMMARY OF THE INVENTION

The present invention relates to a method for the depolymerization of a biomass selected from the group consisting of cellulose, hemicelluloses, lignocelluloses and mixtures thereof. The depolymerization method comprises dissolving the biomass in a homogeneous solution comprising an ionic liquid solvent and an ionic liquid catalyst. The depolymerization reaction rates are facilitated by heating and stirring of the ionic liquid solvent and ionic liquid catalyst solution.

In particular, this invention describes the conversion of dissolved cellulose into reducing sugars (e.g. glucose, fructose, glyceraldehyde, lactose, arabinose, and maltose) and other dehydration products using an ionic liquid as a cellulose solvent and another ionic liquid as a depolymerization catalyst. Current methods of conversion of biomass to carbohydrates use either heterogeneous catalysts or mineral acids, which can be costly, have a limited lifetime, and cannot be recycled. Recently, ionic liquids have been utilized in the process of conversion either as a pretreatment for traditional methods or as a solvent for cellulose which is then reacted with a mineral acid. The invention illustrates the use of an ionic liquid catalyst instead of metal catalysts, enzymes, or mineral acids for the conversion of cellulose to reducible sugars. The reducing sugars can degraded into hydromethylfurfural and furfural, which can then be further degraded in levulinic acid.

The use of an ionic liquid catalyst in the hydrolysis has the advantages of being safer to handle then concentrated mineral acids and does not require the controlled environment that enzymes need to function. Factors like temperature, time, ionic liquid solvent properties, and ionic liquid catalyst structure and composition govern the conversion of biomass to dehydration products and give unprecedented control of the product stream.

DETAILED DESCRIPTION

The conversion of dissolved cellulose into reducing sugars and other products is a technique by which the dissolved cellulose reacts more readily with a Brønsted acid derived ionic liquid. The ionic liquid solvent does this by disrupting the hydrogen bonded supramolecular structure of the cellulose allowing the ionic liquid catalyst to hydrolysis the β-glycosidic bonds producing small glucose oligimers and various reducing sugars. The combination of the ionic liquid solvent and ionic liquid catalyst results in a homogeneous solution increasing the efficiency of the conversion of cellulose into dehydration products.

As used herein the term "ionic liquid solvent" refers to a liquid that is comprised of cations and anions. Ionic liquids are attractive solvents as they are non-volatile, non-flammable, have a high thermal stability, are relatively inexpensive to manufacture, are environmentally friendly, and can be used to provide greater control and flexibility in the overall processing methodology. Ionic liquids solvents of interest exist as liquids well below room temperature up to a temperature as high as 200° C. Preferably, the ionic liquids have melting points at or below 150° C., more preferably, below about 100° C. A generic diagram of an imidazolium based ionic liquid is given in FIG. 1 (left), where R=$C_nH_{2n+1}$. U.S. Pat. No. 7,671,178, issued on Mar. 2, 2010, and incorporated herein by reference, contains numerous examples of suitable ionic liquid solvents for use in the present invention. Preferably, the ionic liquid solvents used herein can fully or partially dissolve the biomass with limited degradation of the biomass.

Figure 1:
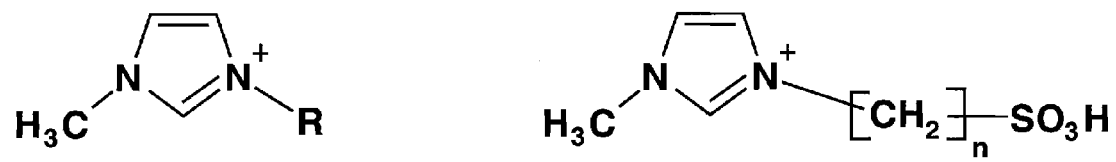
FIG. 1 is a general diagram of the cations of the imidazolium class of ionic liquids (left) and the ionic liquid catalyst (right), where R=$C_nH_{2n+1}$

As used herein the term "ionic liquid catalyst" refers to a ionic liquid consisting of a cation and anions wherein the cation has a Brønsted acid functional group attached giving the structure shown in FIG. 1 (right). The cation of the ionic liquid is not limited to imidazolium but can be ammonium, phosphonium, pyrrolidinium, piperidinium, or pyrimidium. An ionic liquid with just such functionality has been synthesized and has been proven to work in acid catalyzed reactions. See, e.g., A. C. Cole, J. L. Jensen, I. Ntai, K. L. T. Tran, K. J. Weaver, D. C. Forbes and J. H. J. Davis, *J. Am. Chem. Soc.*, 2002, 124, 5962-5963. This ionic liquid contains a protonated sulfonate group which provides the necessary acidic functionality. Preferably, the ionic liquid catalysts have melting points at or below 150° C., more preferably, below about 100° C. The ionic liquid catalyst effects a change in the rate of the depolymerization of the biomass into degradation products but is not consumed by the reaction itself.

The synthesis of the zwitterion was described by M. Yoshizawa, M. Hirao, K. Ito-Akita and H. Ohno, *J. Mater. Chem.*, 2001, 11, 1057-1062; with the conversion to an ionic liquid described by Davis, et al A. C. Cole, J. L. Jensen, I. Ntai, K. L. T. Tran, K. J. Weaver, D. C. Forbes and J. H. J. Davis, *J. Am. Chem. Soc.*, 2002, 124, 5962-5963, both of which are incorporated herein by reference. The ionic liquid catalyst was synthesized by dropwise addition of 1,4-butane sultone (a cyclic sulfur containing compound analogous to a lactone) to a solution of 1-methylimidazole in toluene. As the zwitterion is produced it phase separates from the toluene. The mixture is allowed to react overnight. After reaction, the product is washed several times with ether and toluene to remove any unreacted starting material. The solid is then dried under vacuum. The solid product is then reacted with a stoichiometric amount of acid, in this case trifluoromethanesulfonic acid. The solution is stirred overnight. The ionic liquid catalyst is then washed with toluene and ether to remove any unreacted acid and then dried under vacuum. The product is identified by NMR spectroscopy. The catalyst is not limited to 1,4-butane sultone as a reactant but any alkyl sultone can be used to synthesis the catalyst. Several examples follow of the use of the ionic liquid catalyst in the hydrolysis of cellulose to reducing sugars.

General Procedure for the Hydrolysis of Cellulose Utilizing an Ionic Liquid Solvent and Ionic Liquid Catalyst In a 60 mL glass bottle, 15 g of a 10 wt % microcrystalline cellulose in 1-ethyl-3-methylimidazolium chloride solution was heated to 100° C., then 0.215 g of water and 1 g of 1-methyl-3-(butyl-4-sulfonic acid)imidazolium triflate were added to the heated cellulose solution and stirred for 24 hours. The reaction progress was monitored by removal of 1.0 g aliquots of the reaction mixture at regular intervals.

In order to obtain the concentrate of reducing sugars at a given time, the aliquots were reacted with Benedict's reagent at 100° C. The Benedict's test monitors the reduction of Cu(II) to Cu(I) which results in a color change. After a reaction time of one hour, neocuproine was added to the mixture. The addition of the neocuproine heightens the color change for ease of measurement. Neocuproine is a ligand that complexes Cu(I). The wavelength used to monitor the Cu(I)-neocuproine complex was 454 nm. The mixture was heated to 100° C. for one hour. The mixture was allowed to cool then filtered using a 1.6 μm syringe filter. A 60 μL aliquot was taken and diluted to 10 mL. The solution was then filtered again using a 0.45 μm syringe filter and the absorbance was measured. From the absorbance measurement of the complex solution, the concentration of the reducing sugars could be calculated.

1. Important Conversion Variables

There are several variables that will affect the products from the hydrolysis of cellulose: catalyst, temperature, co-catalyst, and dissolution solvent.

Figure 2:
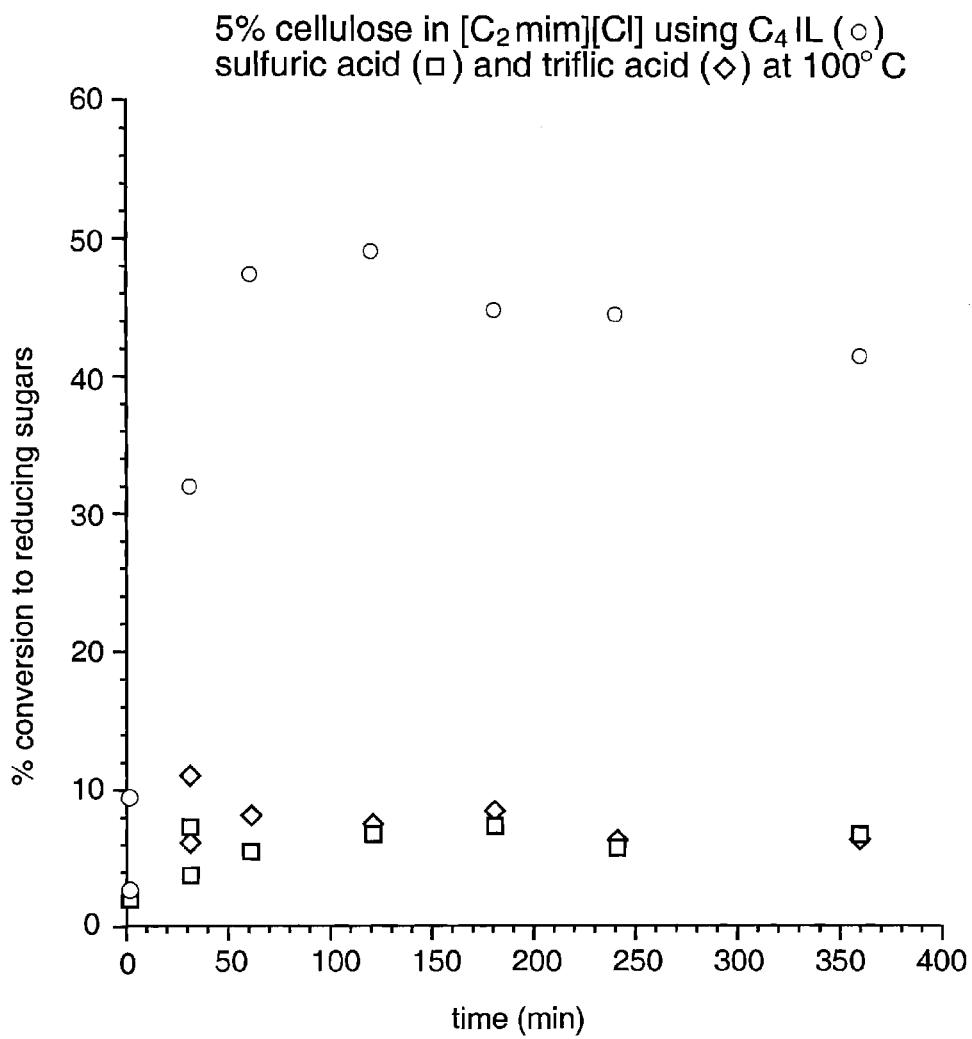
FIG. 2 is a plot of conversion of cellulose to reducing sugars using $C_4IL$ (○), sulfuric acid (□), or triflic acid (◇) at 100° C. in 1-methyl-3-ethylimidazolium chloride.

1A. Hydrolysis of Cellulose using 1-methyl-3-(butyl-4-sulfonic acid) imidazolium triflate or mineral acids Reactions were carried out using the 1-methyl-3-(butyl-4-sulfonic acid) imidazolium triflate ionic liquid ("IL") catalyst as well as mineral acids, $H_2SO_4$ and triflic acid for comparison. Sulfuric acid was used because it is the traditional acid of choice for the hydrolysis of cellulose. Triflic acid was used to confirm that excess acid from the synthesis of the IL catalyst was not responsible for the hydrolysis of the cellulose. The results of the initial reaction of cellulose with the IL catalyst and mineral acids are shown in FIG. 2. The results show that the IL catalyst is more effective at converting the cellulose into reducing sugars than the mineral acids. The decrease in reducing sugars after 2 hrs is due to the slow degradation of the reducing sugars in the reaction solution. Similar results have been observed using mineral acid catalysts in water and in ionic liquids. The reducing sugars are degraded into hydromethylfurfural and furfural, which can then be further degraded in levulinic acid.

Figure 3:
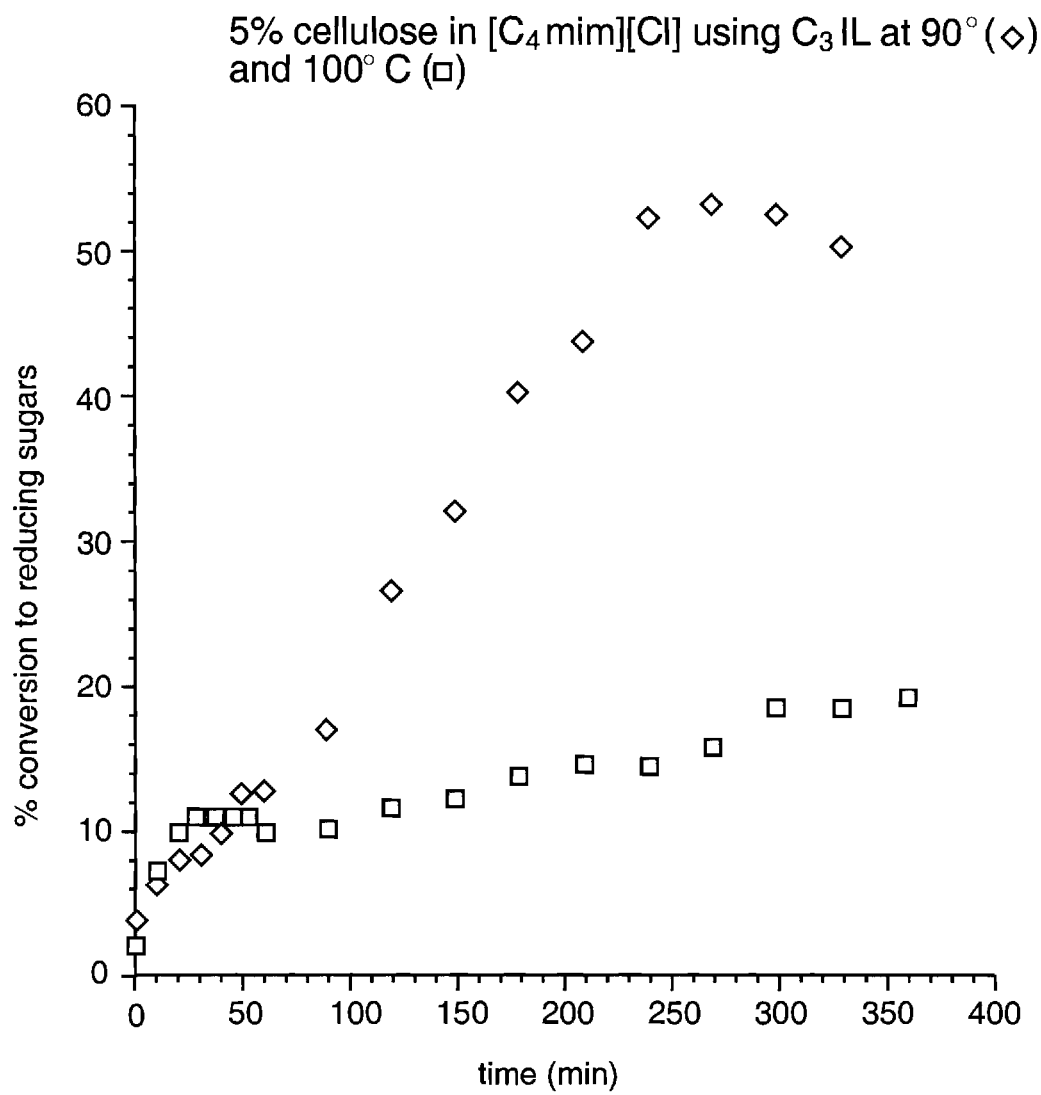
FIG. 3 is a plot of the conversion of cellulose to reducing sugars using $C_3IL$ at 90° C. (◇) and 100° C. (□) in 1-methyl-3-butylimidazolium chloride.

1B. Effects of Temperature on the Hydrolysis of Cellulose using the Ionic Liquid Catalyst It is know that temperature affects reaction kinetics. In order to control the degradation of the reducing sugars, a set of experiments were performed at two different temperatures, 90° C. and 100° C. The results of these experiments are illustrated in FIG. 3. The higher temperature produced a higher conversion of cellulose to reducing sugars initially (under 60 minutes) then the conversion levels out. The decrease in conversion to reducing sugars is due to the increased degradation of the sugars into other products, such as HMF. The lower temperature reaction shows a continued increase in sugar produce until about 4 hours into the reaction at this point the sugar is degraded into HMF and other degradation products. These results illustrate that the production of reducing sugars is increased with temperature but the further gradation of the reducing sugars into other dehydration products is also increased. The hydrolysis of cellulose into reducing sugars can be controlled through the manipulation of the reaction temperature.

1C. Effects of Ionic Liquid Acid Catalyst on the Hydrolysis of Cellulose

Figure 4:
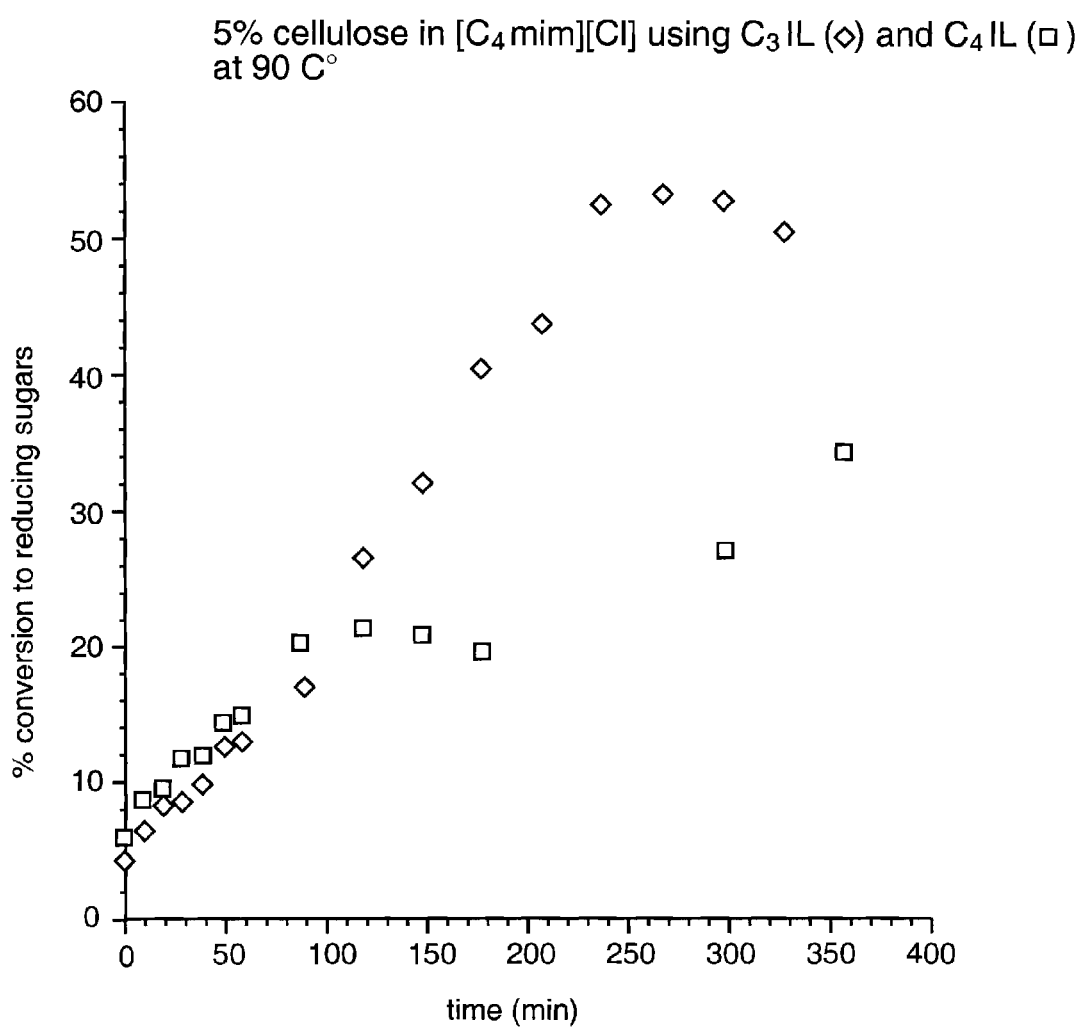
FIG. 4 is a plot of the conversion of cellulose to reducing sugars using $C_3IL$ (◇) and $C_4IL$ (o) at 90° C. in 1-methyl-3-butylimidazolium chloride.

Another important variable to consider is the effect of changes in the catalyst on the hydrolysis of cellulose in an ionic liquid. A comparison of the hydrolysis of cellulose in 1-methyl-3-butylimidazolium chloride at 90° C. using two different catalysts, 1-methyl-3-(propyl-3-sulfonic acid) imidazolium triflate and 1-methyl-3-(butyl-4-sulfonic acid) imidazolium triflate, is shown in FIG. 4. The longer chain catalyst has slightly higher conversion in the beginning, up to 100 minutes, then the conversion tapers off. While the conversion of cellulose using the shorter chain catalyst continues to increase until the side reaction resulting in further degradation begins. This comparison illustrates the ability to control the reaction products though modification of the ionic liquid acid catalyst.

1D. Effects of Ionic Liquid Solvents on the Hydrolysis of Cellulose

Figure 5:
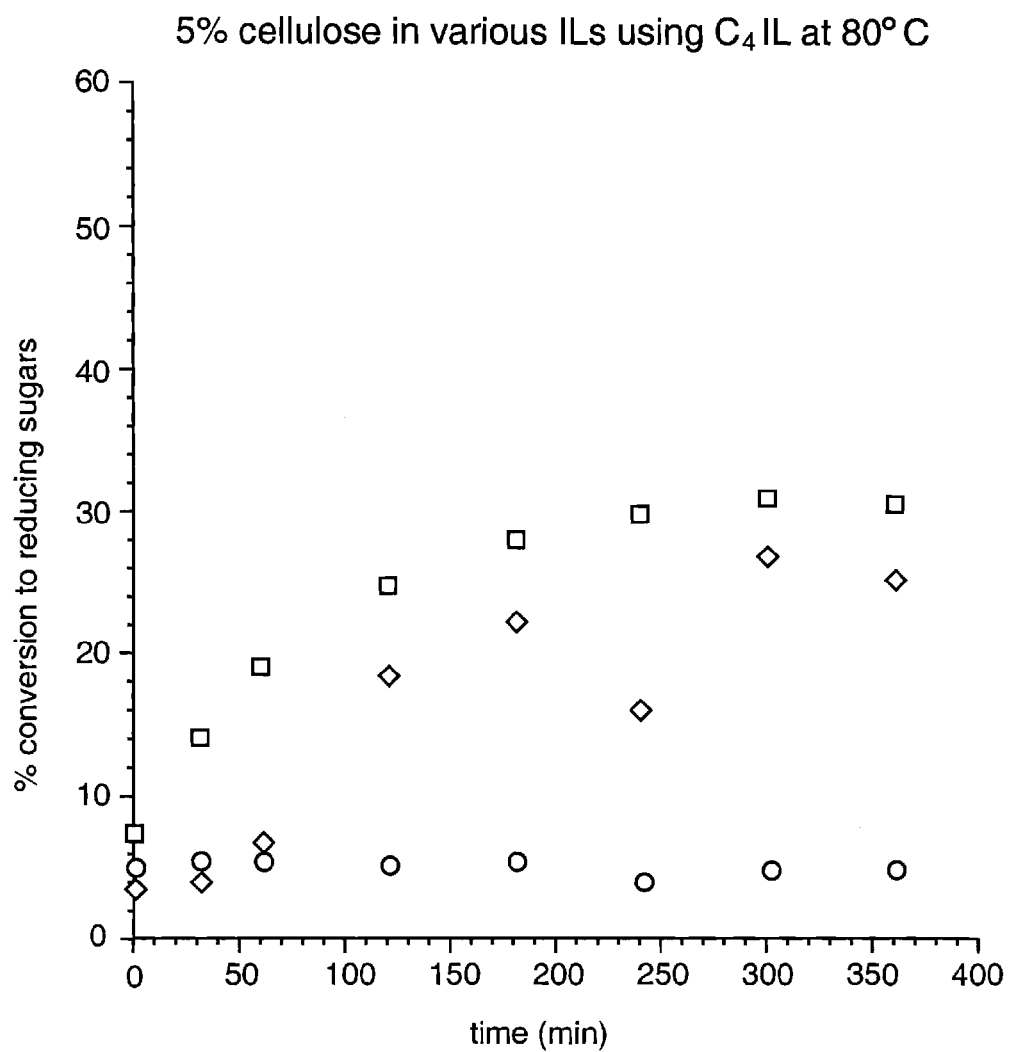
FIG. 5 is a plot of the conversion of cellulose to reducing sugars using $C_4IL$ at 80° C. in 1-methyl-3-allylimidazolium chloride (◇), 1-methyl-3-ethylimidazolium chloride (□), or 1-methyl-3-ethylimidazolium acetate (○).

The effect of ionic liquid solvent on the hydrolysis of cellulose at 90° C. is illustrated in FIG. 5. The figure shows that the ionic liquid, 1-methyl-3-ethylimidazolium chloride, gives a marginally better conversion then the other ionic liquids studied. The ionic liquid, 1-methyl-3-ethylimidazolium acetate gave the lowest conversion of cellulose to reducing sugars; this is most likely due to leveling of the acidity of the ionic liquid acid catalyst by the acetate ion. For the dissolution of cellulose the anion of the ionic liquid has to a good hydrogen bond acceptor in order to break the hydrogen bonds between the cellulose polymer chains. In choosing an ionic liquid for the solvent in the hydrolysis of cellulose, the anion plays an equally important role. The anion must be able to disrupt the hydrogen bond in the cellulose but not interfere with the catalyst through interactions with the acid functional group as in the case with the acetate ionic liquid. The depolymerization reaction rates can be manipulated through charging in the ionic liquid solvent used to dissolve the biomass.

While this invention has been described with respect to exemplary embodiments of the invention, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method for the depolymerization of a biomass selected from the group consisting of cellulose, hemicelluloses, lignocelluloses and mixtures thereof, comprising dissolving the biomass in an homogeneous solution comprising an ionic liquid solvent and an ionic liquid catalyst.

2. A method according to claim 1 wherein said ionic liquid catalyst is an ionic liquid comprised of cations and anions with a melting point below 150° C. that effects a change in the rate of the depolymerization of the biomass into degradation products but is not consumed by the reaction itself.

3. A method according to claim 1 wherein said depolymerization of biomass dissolved in an ionic liquid solvent results in degradation products selected from the group consisting of glucose, fructose, glyceraldehyde, lactose, arabinose, maltose, hydroxymethylfurfural, furfural, levulinic acid, and mixtures thereof, wherein the depolymerization reaction rates are facilitated by heating and stirring of the biomass, the ionic liquid solvent and ionic liquid catalyst solution.

4. A method according to claim 3 wherein said biomass is cellulose.

5. A method according to claim 4 wherein the degradation products are selected from the group consisting of glucose, fructose, glyceraldehyde, lactose, arabinose, and maltose.

6. A method according to claim 4 wherein said ionic liquid solvent is selected from the group consisting of 1-methyl-3-ethylimidazolium chloride, 1-methyl-3-ethylimidazolium acetate, 1-methyl-3-butylimidazolium chloride, 1-methyl-3-butylimidazolium acetate, and mixtures thereof.

7. A method according to claim 4 wherein said ionic liquid catalyst is selected from the group consisting of 1-methyl-3-(propyl-4-sulfonic acid)imidazolium triflate, 1-methyl-3-(butyl-4-sulfonic acid)imidazolium triflate, and mixtures thereof.

8. A method according to claim 4 wherein said ionic liquid catalyst is 1-methyl-3-(butyl-4-sulfonic acid)imidazolium triflate.

* * * * *